United States Patent [19]

Quay

[11] Patent Number: 4,637,929

[45] Date of Patent: Jan. 20, 1987

[54] FERRIOXAMINE-PARAMAGNETIC CONTRAST AGENTS FOR MR IMAGING, COMPOSITION, APPARATUS AND USE

[75] Inventor: Steven C. Quay, Menlo Park, Calif.

[73] Assignee: Salutar, Inc., Sunnyvale, Calif.

[21] Appl. No.: 688,733

[22] Filed: Jan. 4, 1985

[51] Int. Cl.$^4$ .................. A61K 49/00; A61B 5/05; A61B 6/00

[52] U.S. Cl. ........................ 424/9; 436/173; 436/806; 128/653; 128/654; 556/146

[58] Field of Search ............ 424/9; 128/653, 654; 556/40, 146, 147, 148; 436/173, 806

[56] References Cited

U.S. PATENT DOCUMENTS 3,471,476 10/1969 Gaeumann et al. ............... 556/146

FOREIGN PATENT DOCUMENTS 8633082 1/1983 Australia.

OTHER PUBLICATIONS

Pykett, I., Scientific American, May 1982, pp. 78–88.

*Primary Examiner*—Christine M. Nucker
*Assistant Examiner*—Stephen C. Wieder
*Attorney, Agent, or Firm*—Sprung Horn Kramer & Woods

[57] ABSTRACT

The Ferrioxamine (FOM) family of chelates and amide homologs thereof provide excellent contrast agents for magnetic resonance (MR) imaging. The magnetic dipole generated by unpaired electrons within the paramagnetic Fe(III) atoms, cause a local reduction in the bulk magnetic field $B_z$ of the MR system. The resulting shorting of the T1 (spin lattice) relaxation time in the local hydrogen protons within the area of interest, causes an intense "free induction signal" and a corresponding modulation in the collected scanning data. The contrast agent within the tissue or organ of interest causes the tissue to appear on the MR display as a high intensity or white area. Background tissue is displayed as darker or lower intensity greys.

FOM does not penetrate the blood-brain-barrier under normal circumstances; and is therefore useful in detecting the extravasation of arterial blood in the extravascular space during cerebral hemorrhaging and in the endema fluid surrounding tumors. The amide homologs form functional groups which enable the FOM contrast agents to go into solution readily, and promote organ selectivity.

24 Claims, 10 Drawing Figures

STEP 1  PROVIDING
            CONTRAST AGENT

STEP 2  INTRODUCING
            CONTRAST AGENT

STEP 3  WAITING
            FOR IN VIVO
            DISTRIBUTION

STEP 4  IMAGING
            SUBJECT TO OBTAIN
            ENHANCED IMAGE

FIG. 5

FERRIOXAMINE-PARAMAGNETIC CONTRAST AGENTS FOR MR IMAGING, COMPOSITION, APPARATUS AND USE

TECHNICAL FIELD

This invention relates to MR Ferrioxamine contrast agents, and more particularly to FOM family and amide homologs thereof.

BACKGROUND

Heretofore Fe(III) chelates have been employed in paramagnetic contrast agents in the form of DTPA-Fe 3.

SUMMARY

It is therefore an object of this invention to provide improved Ferrioxamine contrast agents for MR imaging.

It is another object of this invention to provide MR Ferrioxamine contrast agents having a high stability, a low toxicity and which are physiologically tolerable.

It is a further object of this invention to provide Ferrioxamine contrast agents in pharmacological form with a low osmolarity.

It is a further object of this invention to provide Ferrioxamine contrast agents which are in vivo responsive.

It is a further object of this invention to provide Ferrioxamine contrast agents which are organ selective.

It is a further object of this invention to provide Ferrioxamine contrast agents which reveal disruption of the normally intact blood-brain-barrier, as occurs in events such as tumors, trauma, and infection.

It is a further object of this invention to provide a method of using such Ferrioxamine contrast agents.

It is a further object of this invention to provide an MR system employing such Ferrioxamine contrast agents.

Briefly, these and other objects of the present invention are accomplished by providing a chemically stable physiologically tolerable FOM contrast agent in a pharmacological state, for in vivo use during diagnostic magnetic resonance (MR) imaging. The contrast agent enhances the MR image of a subject within the MR scanning magnetic field. The paramagnetic metal ion Fe(+3) locally affects the MR scanning magnetic field to reduce the T1 relaxation time of local protons within the subject. The contrast agent contains a Ferrioxamine chelator (FOM) securely bonded around the Fe(+3) ion at six coordination points. FOM-B has the form:

for chemically isolating the heavy metal Fe(+3) ion from the in vivo environment. Homologs of the FOM family of contrast agent contain a functional amide group "A" of the form:

$$A = -C(=O)-N(H)-(CH_2)_{(n-1)}-CH_3$$

wherein "n" is an integer from 0 to 18 indicating the number of Carbon atoms in the Carbon-Hydrogen chain portion of each amide group. The FOM family of contrast agents (and amide homologs) are dispensed in a pharmaceutically acceptable vehicle means such as water. The Carbon-Hydrogen portions of the agent become associated with water of hydration which increases the associated with water of hydration which increases the paramagnetic strength of the contrast agent. The Fe ion has a valence of +3 and produce a contrast agent molecule of zero net charge.

BRIEF DESCRIPTION OF THE DRAWING

Further objects and advantages of the Ferrioxamine (FOM) family of paramagnetic contrast agents, and the method of use thereof, will become apparent from the following detailed description and drawing in which.

Figure 1A:
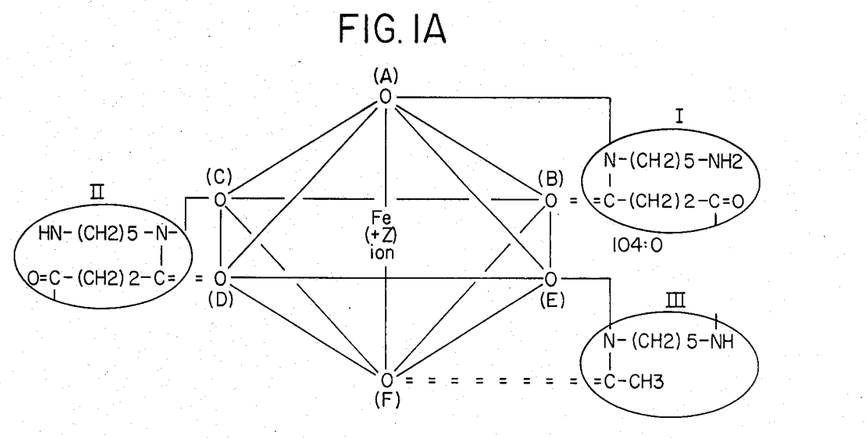
FIG. 1A is a diagram showing the chelate structure of a Ferrioxamine-B (FOM-B) contrast agent.
Figure 1B:
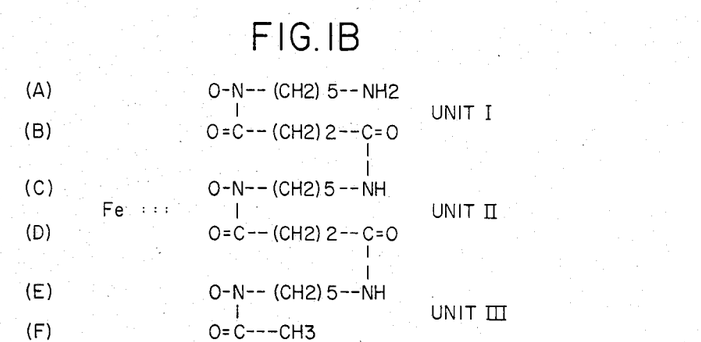
FIG. 1B is a diagram showing the chemical structure of the FOM-B contrast agent of FIG. 1A.
Figure 1C:
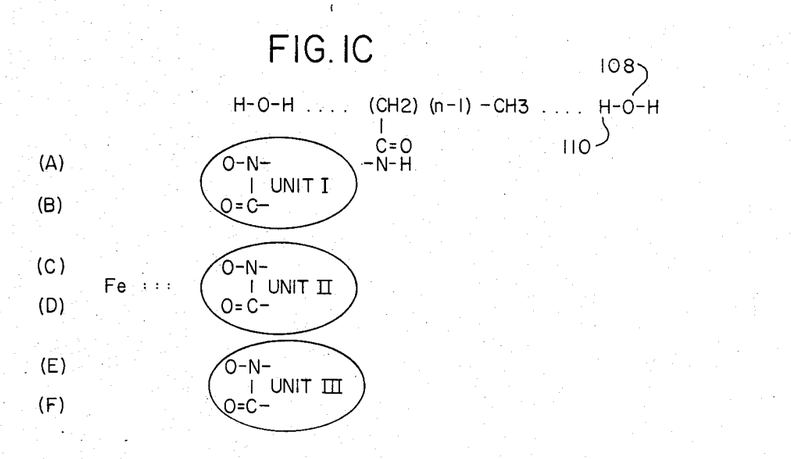
FIG. 1C is a diagram showing the chemical structure of a general Ferrioxamine-amide homolog contrast agent.

FERRIOXAMINE CONTRAST AGENTS (FIGS. 1A 1B 1C)

The present paramagnetic contrast agents are amide homologs of the Ferrioxamine (FOM) chelates A, B, C, D1, D2, E, and F. These FOM chelates are brownish red, and readily soluble in polar solvents such as water and ethanol. Chemically FOMs are related to the sideramycins antibiotic group. Ferrioxamine-B (FOM-B) is the most common and stable member of the FOM family, and has the general chemical name:

N-[5-[3-(5-Aminopentyl hydroxycarbamoyl) propionamido]pentyl]-3[[5-(N-hydroxyamido)pentyl]-carbamoyl] propionohydroxamic acid.

The probable physical chelation structure of the members of the FOM family is a classic octahedron (8 faces, 6 apexes).

FOM-B is shown in Figure 1A. The FOMs are strong chelators having six polar bond coordination points (Oxygens 104), which enclose the paramagnetic Fe(III) ion on all sides.

The amide homologs of FOM-B have the general three unit chemical structure (I, II, III) shown in FIG. 1B. The specific number of carbon atoms in the Carbon- Hydrogen chain portion of the amide group is indicated by "n". The number of Carbons in the methylene CH2 chain between the —CONH— active group and the terminal methylene —CH3, is "n−1".

The amide homologs of Ferrioxamine have the general form:

Amide Homolog of FOM=A-FOM
where A is a general amide group of the form:

and FOM is Ferrioxamine. The particle (osmolarity) to paramagnetic (molar relaxivity) ratio for (FOM-3)(Fe+3) contrast agents is 1:1, and can be prepared in highly concentrated solutions while retaining isotonicity with body fluids.

FIG. 1C shows the tri-unit chemical structure of a general FOM chelate. The water of hydration 108 which collects around the amide CH2 chains offers a reliable source of protons (H+) 110 for resonating with the applied MR fields. Protons 110 have a high probability of being within the local magnetic field variation produced by the paramagnetic Fe ions. These protons form a class of protons for MR imaging which is distinct from random in vivo protons. The prolonged association time of bound water 108, and the close proximity of protons 110 to the Fe ion, establishes a definite and distinct I1 relaxation time which is longer than the I1 for random protons. As a result, protons 110 provided by the water of hydration appear at a higher intensity in the MR image.

AMIDE HOMOLOGS (n=0 to n=18)

The amide family of FOM contrast agents include the normal higher alkyl groups:

| Higher Alkyl Amide | n | Properties of Interest |
|---|---|---|
| Ferrioxamine | 0 | Excellent |
| Methyl-FOM | 1 | renal and |
| Ethyl-FOM | 2 | blood-brain barrier |
| Propyl-FOM | 3 | contrast agent. |
| Butyl-FOM | 4 | Demonstrates |
| Pentyl-FOM | 5 | renal and |
| Hexyl-FOM | 6 | hepatobiliary |
| Heptyl-FOM | 7 | imaging. |
| Octyl-FOM | 8. | |

The single long hydrophobic amide chain, together with the FOM(−3)-Fe(+3), renders the chelate an isosteric substitute for fatty acids. The tissue level of the chelate is high in those organs which have efficient fatty acid uptake systems such as the lepatobiliary system.

Figure 2A:
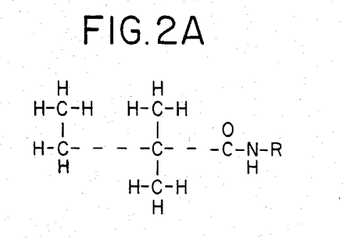
FIG. 2A is a diagram showing the chemical structure of a branched isomer of Pentyl Amide FOM.
Figure 2B:
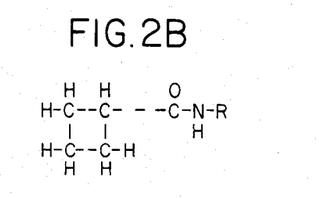
FIG. 2B is a diagram showing the chemical structure of a cyclo isomer of Butyl Amide FOM.

AMIDE HOMOLOG ISOMERS FIGS. 2A and 2B

The amide family of FOMs contrast agents include the higher alkyl groups and the branched and cyclo chain isomers of each group. For example FIG. 2A shows a multi branched isomer of Pentyl-FOM. FIG. 2B shows N-cyclobutyl amide FOM, an isomer of Butyl-FOM.

METHOD OF MANUFACTURE

The fundamental reaction in forming the members of the FOM chelate family is the combining of three molecules of trihydroxamic acid:

around an Fe+3 atom. Crude FOM results from the fermentation of Actinomycetes. The letter designations A, B, C, D1, D2, E, and F refer to the diffusion rates in paper chromatography and ion exchange columns.

One method of forming the various amide homologs is to react the appropriate acylchloride or acid anhydride homolog (HOM) of alkyl carbocyclic acid, to the FOM base forming:

where NH2-R is the initial FOM.

ORGAN SELECTIVE

Venously introduced contrast agents are immediately distributed throughout the circulatory system for imaging. Organs such as the kidney, brain, liver, and heart receive substantial blood flow; and provide selective images which are agent enhanced.

The higher homologs of Amide-FOM tend to be less polar and to bind more to serum proteins, increasing their circulation time. They tend to be extracted from circulation by the liver and excreted in the hepatobiliary system. The amide contrast agent passes through the bile duct (controlled by the ampulla of Vater) and is absorbed into the colon. The Amide contrast agents are suitable for imaging the hepatobiliary (liver-gall bladder) system.

The lower homologs tend to be more polar and remain in solution longer. These homologs are kidney selective and suitable for imaging the kidney, ureter, and bladder.

Oral introduction of the FOM contrast agents requires a higher volume. The agent fills the luminal channel of the digestive system for providing a volume or bulk MR image.

Figure 3A:
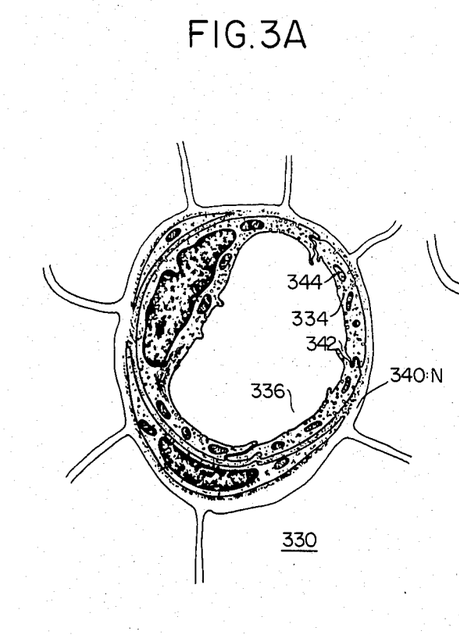
FIG. 3A is a diagram of a normal cerebral arteriole.
Figure 3B:
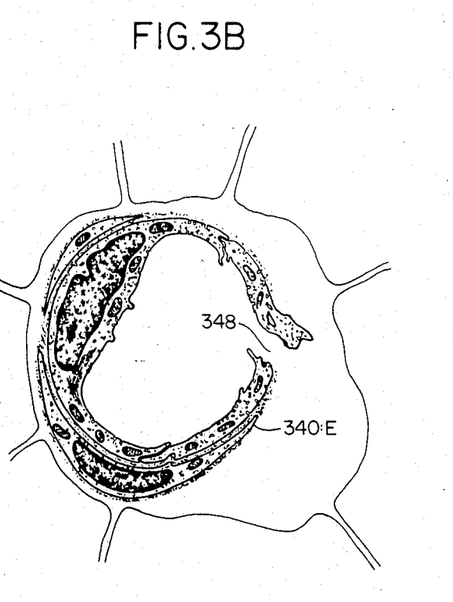
FIG. 3B is a diagram of a cerebral arteriole showing extravascular hemorrhaging.
Figure 4:
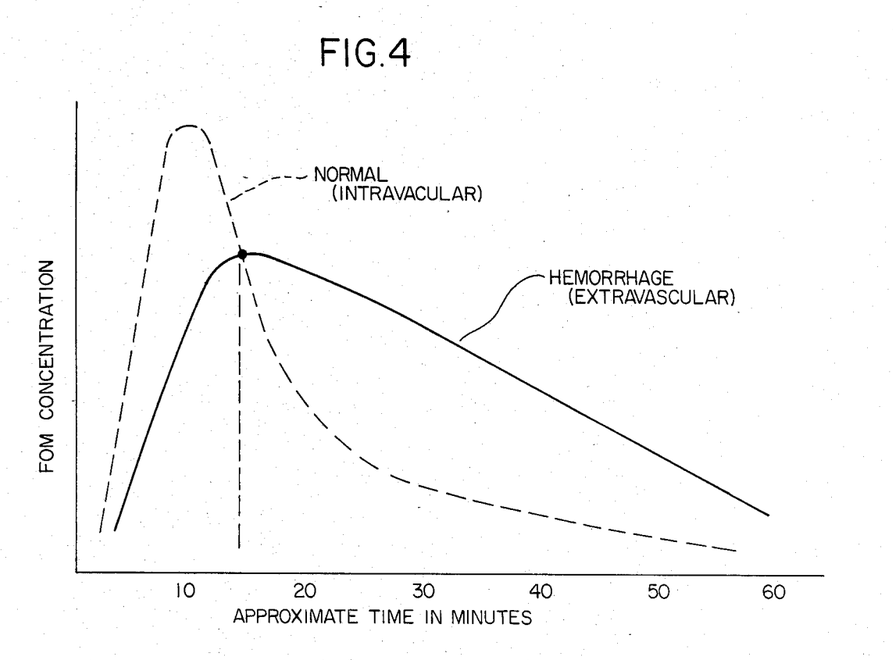
FIG. 4 is a time-FOM concentration chart showing the retention of FOM in the extravascular space after arterial injection of the FOM contrast agent.

CEREBRAL HEMORRHAGE (FIGS. 3A, 3B, and 4)

FIG. 3A shows the cross section of normal arteriole endothelial cell 330 in a human brain. The members of the FOM family (and amides thereof) do not readily pass through basement membrane 334 (the endothelial cell wall), from arteriole lumen 336 into the normally limited extravascular space, 340:N surrounding the arteriole region. The endothelium of the cerebral arterioles and capillaries form a continuous basement membrane of tight inter-endothelial junctions and intra-endothelial marginal fold 342. In addition, pinocytosis of substances through vesicle 344 transport is minimal. The tight permeability properties of the cerebrum endothelial walls define the "blood-brain-barrier" (BBB); and limits the flow of material in order to maintain the homeostasis of the neuronal environment. FOM and other large molecules normally pass through the cerebral vascular system within minutes after venous injection as shown in FIG. 4 (Time verses FOM concentration). The dashed curve "NORMAL (intravascular)" rises and falls sharply.

FIG. 3B shows accumulated arterial blood within enlarged extravascular space 340:E; which has penetrated the BBB through rupture 348 in endothelial wall 334. A portion of the FOM circulating within the vascular system becomes trapped within the enlarged extravascular space. The stagnant nature of enlarged space 340:E causes the FOM in the accumulated blood to be retained for a longer period of time as shown by the solid curve "HEMORRHAGE (extravascular)" of FIG. 4. Traces of the injected FOM may remain in cerebral hemorrhage area for hours before diffusing back into the vascular system.

The paramagnetic properties of the FOM enriched extravascular blood establishes a shorter T1 relaxation time for the local protons within enlarged space 340:E. In the resulting MR image, space 340:E is displayed at a higher intensity, highlighting the accumulated blood.

The luminal blood flow is moving within the vascular system and therefore appears dark (no image). The temporary high serum FOM level in the vascular blood flow is not displayed. The background tissue is unenhanced by FOM and is also dark. An extravascular imaging window developes almost immediately after injection of the FOM contrast agent, and can extend for several hours thereafter. The highest contrast image is obtained when the extravascular FOM reaches its highest concentration. This preferred time for imaging occurs shortly after the peak in intravascular FOM concentration (dashed curve), when the two curves intersect.

FOM highlighted images of cerebral regions are useful in studying hemorrhage, infection and disease processes involving disruption of the BBB. These disease include trauma, both acute and subacute (subdural hemotoma), and tumors, both primary and secondary.

STABLE-POWDER STATE

The stable powder state of the Ferrioxamine (FOM) contrast agents have an indefinite shelf life, and is the preferred state for shipping and storage. The contrast agent in water solution (or other solvent) is packaged in small storage vials, and frozen under a vacuum. The low pressure sublimates the solvent, leaving crystals of the contrast agent. The vial is sealed to prevent entry of contaminants, and to preserve the internal vacuum. The resulting freeze-dried, vacuum sealed powder, is highly stable and free from environmental degradation effects.

PHARMACOLOGICAL-SOLUTION STATE

The stable-powdered contrast agent may be raised to a pharmacological state by the addition of a solvent such as water, serum, albumin solutions, or saline. A typical injectable composition contains about 10 mg human serum albumin (1 percent USP Parke-Davis) with an FOM concentration of and from about 20 to about 200 mg/ml (20–40 mg/ml preferred). A 0.01 M phosphate buffer (pH 7.5) may be employed containing 0.9 percent NaCl. The pH of the aqueous solutions may range between 5–9 (preferably between 6–8) over a volume range of between about 5 ml to about 150 ml (10–30 ml preferred). The storage vial may have twin compartments containing the desired amounts of powdered FOM and solvent for a single application. When the seal between the compartments is broken, the FOM goes into solution at the desired concentration for immediate use. The aqueous solution is also stable in a filtered sterilized state if kept in the dark.

Figure 5:
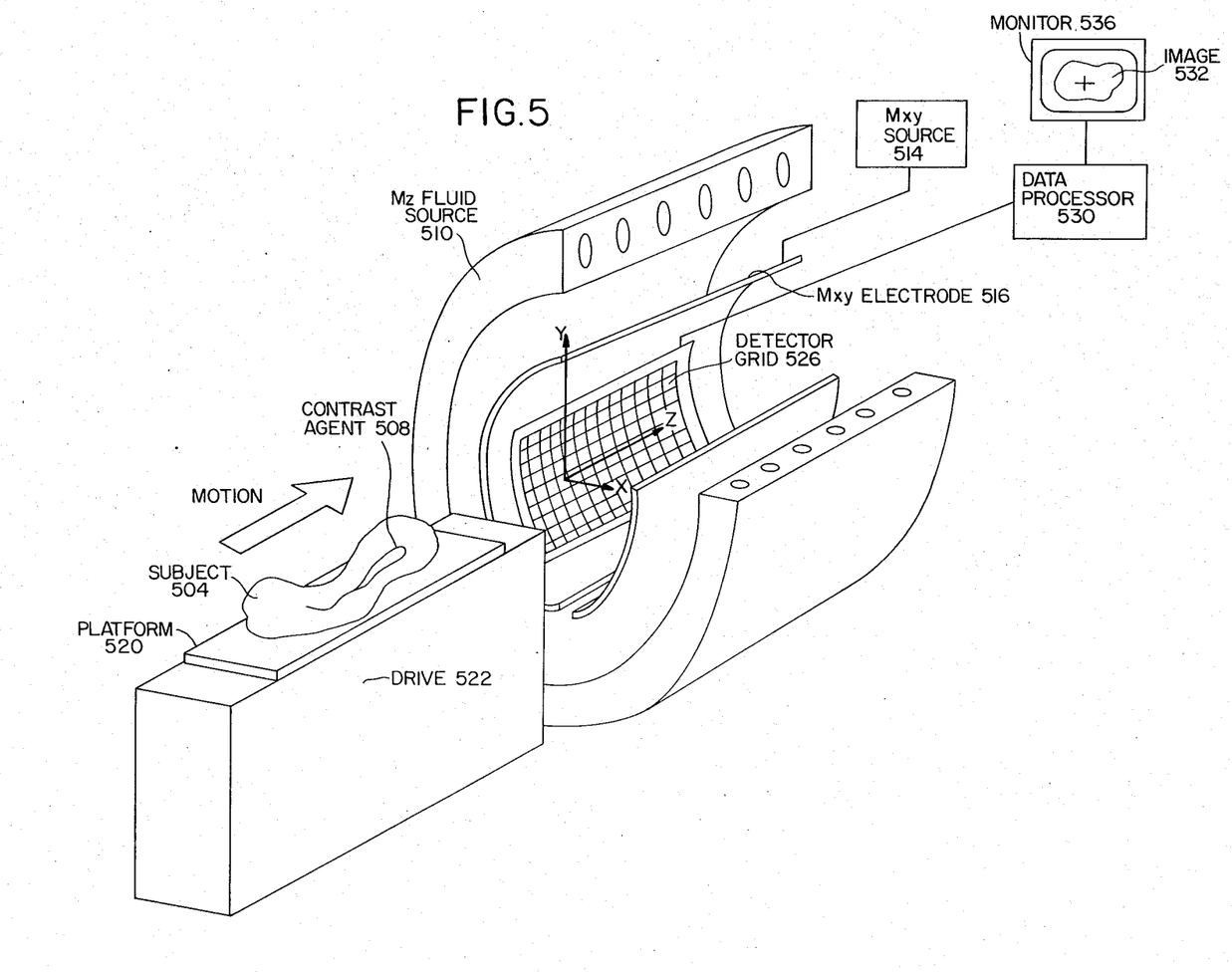
FIG. 5 is a cut-away perspective view of an MR system showing the motion platform and subject using Ferrioxamine paramagnetic contrast agents.

GENERAL MR SYSTEM (FIG. 5)

Magnetic resonance (MR) imaging system 500 has two magnetic components which scan subject 504 for obtaining MR data enhanced by the presence of contrast agent 508. Bulk magnetic field Mz from Z field source 510 causes paramagnetic particles such as local hydrogen protons within the subject to aline with the Z axis. Periodic or rotating field Mxy from XY field generator 514 extends between XY electrodes 516. The subject to be scanned is positioned on support platform 520 and moved through the magnetic fields by drive 522. Rotating field Mxy is tuned to cause resonant precession of the local protons within the tissue of interest. Each local proton precesses about the Z axis in response to a particular frequency of rotating field Mxy. When rotating field Mxy is removed, the precessing protons decay back into alinement with Mz.

The decay period of the local protons (spin lattice relaxation time T1) varies between organs and between conditions within the same organ. Tumor tissue tends to have a longer T1 than healthy tissue. The presence of the paramagnetic metal ions Fe causes a shortening of the proton T1, without substantially affecting T2. The energy of precession is released forming a free induction signal. Grid detector 526 senses the decay signals which are stored and processed by data processer system 530. to form an image 532 on monitor 536.

The imaging system is further disclosed in *Scientific American*, May 1982, pages 78–88, and "NMR A Primer for Medical Imaging" by Wolf and Popp Slack Book Division (ISBN 0-943432-19-7), which disclosures are hereby incorporated by reference.

Figure 6:
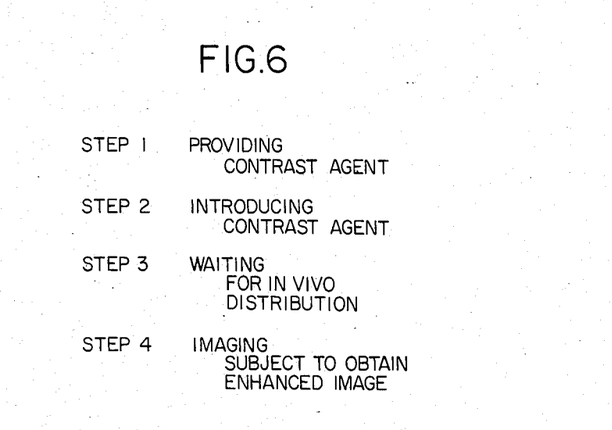
FIG. 6 is a flow chart showing a method of using the Ferrioxamine paramagnetic contrast agents.

METHOD OF USE (FIG. 6)

FIG. 6 shows a method of imaging subject 504 with MR system 500 employing an paramagnetic contrast agent 508.

(Step 1) PROVIDING a physiologically tolerable contrast agent 508 in the form: FOM or amide homolog thereof dispensed in a suitable carrier vehicle.

(Step 2) INTRODUCING the FOM contrast agent into subject 508 orally or by intravenous injection.

(Step 3) WAITING for the FOM to distribute into the organ of interest, and for the amide functional groups to cooperate with the in vivo environment.

(Step 4) IMAGING the subject with MR system 500 to obtain an enhanced MR image.

Extravascular applications have a wide imaging window, and time involved in the waiting step may be short or extensive. Comparison or subtraction imaging, requires an initial step of providing data from a prior MR imaging, and the final step of subtraction comparing the prior MR image with the current MR image. A historical base line image from the subjects file may be employed as the prior image. Alternatively, a current MR image made without the use of a contrast agent may be employed.

INDUSTRIAL APPLICABILITY

It will be apparent to those skilled in the art that the objects of this invention have been achieved as described hereinbefore by providing an improved physiologically tolerable contrast agents with a high stability, and a low toxicity. The contrast agent has a high paramagnetic effect due to the amide water of hydration, and a low osmolarity due to the amide bonding. The variability of the amide structure permits a range of vivo response and organ selection, including surface selectivity of the colon.

CONCLUSION

Clearly various changes may be made in the structure and embodiments shown herein without departing from the concept of the invention. Further, the features of the embodiments shown in the various Figures may be employed with the embodiments of the other Figures.

Therefore, the scope of the invention is to be determined by the terminology of the following claims and the legal equivalents thereof.

I claim as my invention:

1. A chemically stable physiologically tolerable contrast agent in a solid state form, for use in vivo solution during diagnostic magnetic resonance (MR) imaging, to enhance the MR image of the region of interest of a subject within the magnetic field of the MR system, comprising:
   a composition of matter contrast agent having the form:
   A-FOM,
   where:
   FOM is at least one member of the Ferrioxamine family of chelates selected from the group consisting of A, B, C, D1, D2, E, and F, which has a paramagnetic atom of ionized Fe for locally affecting the magnetic field of the MR system securely chelated therein at a plurality of coordination points to chemically isolate the Fe ion from the in vivo environment; and
   A is an amide group of the form having the chemical form:
   A=—NHCO—(CH2)(n−1)—CH3,
   for functionally cooperating with the in vivo environment, wherein "n" is an integer indicating the number of Carbon atoms in the Carbon-Hydrogen portion of the amide group A;
   whereby the contrast agent causes a reduction in the T1 relaxation time near the region of interest within the subject.

2. The contrast agent of claim 1, wherein the Fe ion is Fe(+3) and the A-FOM composition of matter is a molecule having a zero net atomic charge.

3. The contrast agent of claim 1, wherein FOM is the B member of the Ferrioxamine family of chelates.

4. A chemically stable physiologically tolerable contrast agent in a pharmacological solution state, for in vivo use during diagnostic magnetic resonance (MR) imaging, to enhance the MR image of a subject within the magnetic field of the MR system, comprising:
   a composition of matter contrast agent having the form:
   A-FOM,
   where
   FOM is at least one member of the Ferrioxamine family of chelates selected from the group consisting of A, B, C, D1, D2, E, and F, which has a paramagnetic atom of ionized Fe for locally affecting the magnetic field of the MR system securely chelated therein at a plurality of coordination points to chemically isolate the Fe ion from the in vivo environment; and
   A is an amide group covalently bonded to the FOM chelator for functionally cooperating with the in vivo environment, and having the chemical form:
   A=—NHCO—(CH2)(n−1)—CH3,
   wherein "n" is an integer indicating the number of Carbon atoms in the Carbon-Hydrogen portion of the amide group A; and
   a pharmaceutically acceptable vehicle means for dispersing the A-FOM contrast agent;
   whereby the contrast agent causes a reduction in the T1 relaxation time near the region of interest within the subject.

5. The contrast agent of claim 4, wherein the Fe ion is Fe(+3) and the A-FOM composition of matter is a molecule having a zero net atomic charge.

6. The contrast agent of claim 4, wherein FOM is the B member of the Ferrioxamine family of chelates.

7. The contrast agent of claim 4, wherein the amide group A is an amide homolog having a value of "n" from 0 to 18.

8. The contrast agent of claim 7, wherein the amide homolog includes branched isomers thereof.

9. The contrast agent of claim 7, wherein the amide homolog includes cyclo isomers thereof.

10. The contrast agent of claim 4, wherein the vehicle means is a water solution.

11. The contrast agent of claim 10, further comprising water of hydration associated with the Carbon-Hydrogen portion to the amide homolog.

12. The method of imaging a subject with a magnetic resonance (MR) imaging system employing a paramagnetic contrast agent, comprising the steps of:
   PROVIDING a physiologically tolerable contrast agent dispersed in a suitable carrier vehicle, the contrast agent having the form:
   A-FOM,
   where:
   FOM is at least one member of the Ferrioxamine family of chelates selected from the group consisting of A, B, C, D1, D2, E, and F, which has a paramagnetic atom of ionized Fe for locally affecting the magnetic field of the MR system securely chelated therein at a plurality of coordination points for chemically isolating the Fe ion from the in vivo environment; and
   A is an amide group covalently bonded to the FOM chelator for functionally cooperating with the in vivo environment, and having the chemical form:
   A=—NHCO—(CH2)(n−1)—CH3,
   wherein "n" is an integer indicating the number of Carbon atoms in the Carbon-Hydrogen portion of the amide group A; and
   INTRODUCING the A-FOM contrast agent and carrier vehicle into the subject;
   WAITING for the amide functional groups to cooperate with the in vivo environment; and
   IMAGING the region of interest within the subject with the MR system to obtain a contrast agent enhanced MR image.

13. The method of imaging a subject as specified in claim 30, wherein the contrast agent is introduced by intravenous injection.

14. The method of imaging a subject as specified in claim 30, wherein the volume of the injected vehicle and contrast agent is from about 5 ml to about 150 ml, and has an A-FOM concentration of from about 20 mg/ml to about 200 mg/ml.

15. The method of imaging a subject as specified in claim 30, further comprising:
   the initial step of providing data from a prior MR imaging; and the final step of subtraction comparing the prior MR image with the current MR image.

16. The method of imaging a cerebral extravascular region within the brain of a subject with a magnetic resonance (MR) imaging system employing a paramagnetic contrast agent, comprising the steps of:

PROVIDING a physiologically tolerable FOM contrast agent dispersed in a suitable carrier vehicle, where FOM is at least one member of the Ferrioxamine family of chelates selected from the group consisting of A, B, C, D1, D2, E, and F, which has a paramagnetic atom of ionized Fe for locally affecting the magnetic field of the MR system securely chelated therein at a plurality of coordination points for chemically isolating the Fe ion from the in vivo environment;

INTRODUCING the FOM contrast agent into the subject by intravenous injection;

WAITING for the amide functional groups to cooperate with the in vivo environment; and IMAGING the region of interest within a subject with the MR system to obtain a contrast agent enhanced MR image.

17. The method of imaging a cerebral extravascular region within the brain of a subject as specified in claim 16, wherein the contrast agent is introduced by intravenous injection.

18. The method of imaging a cerebral extravascular region within the brain of a subject as specified in claim 16, wherein the volume of the injected vehicle and contrast agent is from about 5 ml to about 150 ml, and has an FOM concentration of from about 20 mg/ml to about 200 mg/ml.

19. The method of imaging a cerebral extravascular region within the brain of a subject as specified in claim 16, wherein the volume of the injected vehicle and contrast agent is from about 10 ml to about 30 ml, and has an FOM concentration of from about 20 mg/ml to about 40 mg/ml.

20. The method of imaging a cerebral extravascular region within the brain of a subject as specified in claim 16, further comprising:

the initial step of providing data from a prior MR imaging: and the final step of comparing the prior MR image with the current MR image.

21. The method of imaging a cerebral extravascular region within the brain of a subject as specified in claim 16, wherein the contrast agent is in the form:

A-FOM where

A is an amide group of the form $A = -NHCO-(CH2)(n-1)-CH3$, wherein "n" is an integer from 0 to 18 indicating the number of Carbon atoms in the Carbon-Hydrogen portion of the amide group A, for functionally cooperating with the in vivo environment.

22. The method of imaging a cerebral extravascular region within the brain of a subject as specified in claim 16, wherein FOM is the B member of the Ferrioxamine family of chelates.

23. The method of imaging a cerebral extravascular region within the brain of a subject as specified in claim 16, wherein the period of waiting involved in the waiting step may be short or extensive, and the imaging step has a wide imaging window.

24. The method of imaging a cerebral extravascular region within the brain of a subject as specified in claim 16, wherein the imaging occurs proximate in time with the maximum concentration of FOM contrast agent within the extravascular region.

* * * * *

UNITED STATES PATENT AND TRADEMARK OFFICE
CERTIFICATE OF CORRECTION

PATENT NO. : 4,637,929

DATED : January 20, 1987

INVENTOR(S) : Steven C. Quay

It is certified that error appears in the above-identified patent and that said Letters Patent is hereby corrected as shown below:   Title page:

| | |
|---|---|
| Abstract, lines 18-19 | After "the" delete "endema" and substitute --edema-- |
| Col. 1, line 14 | After "of" delete "DTPA-Fe 3" and substitute --DTPA-Fe$^{+3}$-- |
| Col. 2, line 15 | After "and" delete "produce" and substitute --produces-- |
| Col. 3, line 22 | After "for" delete "resonanting" and substitute --resonating-- |
| Col. 3, line 31 | After "distinct" delete "Il" and substitute --T1-- |
| Col. 3, line 32 | Before "for" delete "Il" and substitute --T1 -- |
| Col. 3, line 61 | After "a" delete "multi branced" and substitute --multi-branched-- |
| Col. 4, line 51 | After "space" delete "," |
| Col. 4, line 63 | Before "FOM" delete "verses" and substitute --versus-- |
| Col. 6, line 53 | After "the" delete "subjects" and substitute --subject's-- |
| Col. 6, line 63 | After "contrast" delete "agents" and substitute --agent-- |
| Col. 8, line 58 | After "claim" delete "30" and substitute --12-- |

UNITED STATES PATENT AND TRADEMARK OFFICE
CERTIFICATE OF CORRECTION

PATENT NO. : 4,637,929
DATED : January 20, 1987
INVENTOR(S) : Steven C. Quay

It is certified that error appears in the above-identified patent and that said Letters Patent is hereby corrected as shown below:

Col. 8, line 61        After "claim" delete "30" and substitute --12--

Col. 8, line 66        After "claim" delete "30" and substitute --12--

Fig. 4                 After "NORMAL" delete "(INTRAVACULAR)" and substitute --(INTRAVASCULAR)--

Signed and Sealed this

Twenty-second Day of March, 1988

Attest:

DONALD J. QUIGG

Attesting Officer                Commissioner of Patents and Trademarks